United States Patent [19]

Kelly

[11] Patent Number: 5,908,829
[45] Date of Patent: Jun. 1, 1999

[54] USE OF MCP-1 FOR INDUCING RIPENING OF THE CERVIX

[75] Inventor: Rodney William Kelly, Edinburgh, United Kingdom

[73] Assignee: Medical Research Council, London, United Kingdom

[21] Appl. No.: 08/716,188

[22] PCT Filed: Mar. 31, 1995

[86] PCT No.: PCT/GB95/00733

§ 371 Date: Sep. 30, 1996

§ 102(e) Date: Sep. 30, 1996

[87] PCT Pub. No.: WO95/26748

PCT Pub. Date: Oct. 12, 1995

[30] Foreign Application Priority Data

Mar. 31, 1994 [GB] United Kingdom .................... 9406463

[51] Int. Cl.$^6$ .............................. A61K 38/00; C07K 5/00; C07K 7/00
[52] U.S. Cl. ............................................... 514/12; 530/324
[58] Field of Search ............................... 530/324; 514/12

[56] References Cited

U.S. PATENT DOCUMENTS

| 4,870,067 | 9/1989 | Chwalisz et al. ....................... 514/171 |
| 5,192,743 | 3/1993 | Hsu et al. .................................... 514/8 |

FOREIGN PATENT DOCUMENTS

| 0 543 476 | 5/1993 | European Pat. Off. . |
| WO98/08777 | 8/1990 | WIPO . |
| WO92/20372 | 11/1992 | WIPO . |

OTHER PUBLICATIONS

Ibelgaufts, H. *Dictionary of Cytokines* VCH Inc. Weinheim, Germany pp. 147–148, and p. 503.

Hartung, et al.; "Ripening of the Uterine Cervix of the Guinea–Pig after Treatment withthe Progesterone Antagonist Onapristone (ZK 98.299): an Electron Microscopic Study"; Human Reproduction; vol. 4, pp. 369–377; 1989.

Kishimoto, "Interleukin–8 and MCAF: Novel Leukocyte Recruitment and Activating Cytokines"; Molec. Bio.; 1992; vol. 51, pp. 236–265.

Osmers, et al.; "Origin of Cervical Collagenase during Paturition"; Am. J. Obstet Gynecol; May 1992.

Leonard, et al.; "Human Monocyte Chemattractant Protein–1 (MCP–1)"; Immunol. Today; vol. 11, No. 3; 1990.

Junqueira, et al.; "Morphologic and Histochemical Evidence for the Occurrence of Collagenolysis and for the Role of Neutrophilic Polymorphonuclear Leukocytes during Cervical Dilation"; Am. J. Obstet. Gynecol.; Oct. 1, 1990.

Cochran, et al.; "Molecular Cloning of Gene Sequences Regulated by Platelet–derived Growth Factor"; Ceil; vol. 33, pp. 939–946.

Barclay, et al.; "Interleukin–8 Production by the Human Cervix"; Am. J. Obstet Gynecol; 169; pp. 625–631.

Chesterman; "Atheroma: Vessel Wall and Thrombosis"; Cardiovascular Disease; pp. 13.138–13.141.

Callard, et al.; Extract from The Cytokine Facts Book; Academic Press; 1994.

Van Damme, et al.; "Structural and Functional Identification of Two Human, Tumor–derived Monocyte Chemotactic Proteins (MCP–2 and MCP–3) Belonging to the Chemokine Family"; J. Exp. Med.; 176; pp. 59–65.

Yoshimura, et al.; "Interleukin–8 (NAP–1) and Related Cytokines"; Basel, Karger, 1992; vol. 4; pp. 131–152.

Rolfe, et al.; "Expression and Regulation of Human Pulmonary Fibroblast–derived Monocyte Chemotactic Peptide–1"; Am J Physiol; 263; pp. L–536–L–545.

Yoshimura, et al.; "Secretion by Human Fibroblasts of Monocyte Chemoattractant Protein–1, the Product of Gene JE"; J Immunol; 144; pp. 2377–2383.

Yoshimura, et al.; "Human Monocyte Chemoattractant Protein–1 (MCP–1)"; FEBS Letters; 244; pp. 487–493.

Kelly, et al.; Progesterone Control of Interleukin–8 Production in Endometrium and Chorio–decidual Cells Underlines the Role of the Neutrophil in Menstruation and Parturition; Human Reproduction; 9, pp. 253–258.

Kelly, et al.; Choriodecidual Production of Interleukin–8 and Mechanism of Parturition; Lancet; vol. 339; Mar. 1992; pp. 776–777.

Abstract; JP–05271092–A.

*Primary Examiner*—Avis M. Davenport
*Attorney, Agent, or Firm*—Nixon & Vanderhye P.C.

[57] ABSTRACT

Monocyte chemotactic peptide-1 or a functional derivative thereof is useful in inducing cervical ripening, for example for; (A) induction of labor at term, (B) induction of labor in connection with a pathological pregnancy, (C) induction of labor in connection with intrauterine fetal death, (D) induction of abortion, (E) induction of preterm labor, (F) induction of cervical ripening of a non-pregnant female or pregnant female to assist for surgical or diagnostic procedure, and (G) induction of cervical ripening for female to be treated by in vitro fertilisation.

8 Claims, No Drawings

USE OF MCP-1 FOR INDUCING RIPENING OF THE CERVIX

BACKGROUND OF THE INVENTION

1. Field of the Invention

This invention relates to a treatment for ripening of the cervix, particularly in the induction of labour to assist mammals to give birth.

2. Description of the Related Art

Parturition (expulsion of the fetus from the uterus), requires both contractions of the myometrium, the smooth muscle of the uterus, and a softening of the highly connective tissue of the cervix, so that it will stretch and dilate sufficiently to allow the fetus to be expelled. This softening is known as "ripening".

The current preferred method of cervical ripening is by the use of prostaglandin E2. This is used as a vaginal gel or tablet or as a gel placed in the cervix. One worry about the use of $PGE_2$ is that there is a possibility of hyper-stimulation of the uterus, leading to myometrial contractions before the cervix is ripened and therefore before a comfortable or safe birth is possible. The ideal preparation would soften and efface the cervix without causing myometrial contractions. This would allow the subsequent contractions (inducible if necessary with a small dose of prostaglandin) to deliver the baby with a minimum of resistance.

There is good evidence from animal experiments that the antiprogestins such as RU486 would meet these requirements, but the problem with this drug is that it has associated antiglucocorticoid activity leading to elevated cortisol and ACTH levels [X. Bertagna et al. J Clin Endocrinol Metab 78, 375–380 (1994)] and might also be detrimental to the fetus.

The use of interleukin-8 has also been proposed previously as an agent to ripen the cervix (WO 93/09796). It is known that IL-8 production is suppressed by progesterone [R W Kelly et al, The Lancet, 339, 776–777 (1992); R W Kelly et al. Human reproduction 9, 253–258 (1994)].

SUMMARY OF THE INVENTION

It has now surprisingly been found that monocyte chemotactic peptide-1 (MCP-1) production by choriodecidual tissue is inhibited by progesterone. Choriodecidual tissue is that found on the outside of the fetal sac and therefore in contact with the uterus in the cervical region. It follows that MCP-1 and its functional derivatives can be used for cervical ripening.

The invention accordingly provides the use of a monocyte chemotactic peptide-1 (MCP-1) or a functional derivative thereof in the manufacture of a medicament for inducing ripening of the cervix of a female mammal. The female mammal can be a human being or an animal. Typically it is a female human. MCP-1 or a functional derivative thereof can thus be used in assisting mammalian birth or fetal removal.

MCP-1 or a functional derivative thereof can initiate a localised action and not induce the excessive myometrial contractility sometimes associated with the use of prostaglandin. They would not therefore prejudice the fetus. During birth the cervix normally ripens without help from outside. However, the compounds of the invention can help during the normal ripening and during all birth situations in which ripening is not sufficient. Further they will support normal ripening to make the birth process easier for the women. There can therefore be a reduction or avoidance of pain during birth, abortion and surgical and diagnostic treatment.

DESCRIPTION OF THE PREFERRED EMBODIMENTS

MCP-1, also known as monocyte chemotactic and activating factor (MCAF) can be obtained from fibroblasts or monocytes [T Yoshimura et al. FEBS Letters, 244, 487–493; T Yoshimura et al J Immunol 144, 2377–2383 (1990); M W Rolfe et al, Am J Physiol 263 L536–L545 (1992)]. MCP-1 can be obtained by recombinant DNA synthesis or by peptide synthesis using a modification of the procedure for IL-8 synthesis [I Clark-Lewis, Biochemistry, 30 3128–3135 (1991)]. MCP-1 can also be obtained from biological sources such as polyI/polyC stimulated fibroblasts in culture. Natural variants of MCP exist due to different carbohydrate substitution. The peptide has a terminal sialic acid residue and a degree of O-glycosylation which gives rise to different molecular weight species [T Yoshimura, in: Baggiolini M and Sorg, C "Interleukin-8 (NAP-1) and related cytokines" Karger, Basel, 131–152 (1992)].

A "functional derivative" of MCP-1 is also capable of inducing cervical ripening. That may be determined by testing. The term "functional derivative" is intended to include "fragments", "variants", "analogues", "chemical derivatives" or "polymeric forms" of MCP-1. A "fragment" is a shortened form of MCP-1. A fragment may typically contain from 6 to n−1 residues where n is the number of amino acid residues of the native molecule. A fragment may therefore consist of 6 to 50, for example from 10 to 40 or 15 to 25, residues.

A "variant" refers to a naturally occurring molecule substantially similar to either MCP-1 or a fragment thereof. Examples are the tumour-derived variants called MCP-2 and MCP-3 [J van Damme et al. J Exp Med 176, 59–65 (1992)]. An "analogue" of MCP-1 is a non-natural molecule substantially similar to either MCP-1 or a fragment thereof. A molecule is said to be "substantially similar" to another molecule if the sequence of amino acids in both molecules is substantially the same and if both molecules possess a similar biological activity.

A "chemical derivative" of MCP-1 contains additional chemical groups not normally a part of the molecule. Such chemical groups may improve the molecule's solubility, absorption, biological half-life, etc. They may alternatively decrease the toxicity of the molecule or eliminate or attenuate any undesirable side effect of the molecule. Examples of chemical groups giving rise to such effects are disclosed in Remington's Pharmaceutical Sciences (1980) and will be apparent to those of ordinary skill in the art. Polymeric forms of MCP-1 are those having repeated units of the monomeric form. Such forms appear to exist in solution.

A MCP-1 is a β-chemokine or C-C chemokine. Any β-chemokine may be employed in the present invention. Thus, β-chemokines other than MCP-1 can be viewed as functional derivatives of MCP-1. Typically a human β-chemokine is used in the treatment of a human female. An animal β-chemokine could be used to treat a human female if compatible therewith. That may be determined by testing. Preferred β-chemokines that may be used in the present invention are:

human MCP-1, human MCP-2, human MCP-3;

human RANTES;

human MIP-1α, human MIP-1β; and

I-309 (Table 1, SEQ ID NO:s 2–7 and 1, respectively).

These β-chemokines are detailed in "The Cytokine Facts Book" by R. Callard and A. Gearing, Academic Press, London, 1994. Their amino acid sequences are set out in Table 1 below. The β-chemokines are all chemotactic for monocytes. The in vitro biological functions of MCP-1, MCP-2, MCP-3, RANTES, MIP-1α, MIP-1β and I-309 are shown in Table 2 below. I-309 is the human homologue of the murine TCA-3 gene [S. D. Wilson et al. J. Immunol 145, 2745–2744 (1990); M. D. Miller et al. J. Immunol 143, 2907–2916 (1989); P. R. Burd et al. J. Immunol 139, 3126–3131 (1987)].

A fragment of a β-chemokine may be employed in the present invention. The fragment must be capable of inducing ripening of the cervix. That may be determined by testing. Suitable fragments may contain from 6 to n−1 amino acid residues where n is the number of amino acid residues of the β-chemokine. A fragment may therefore consist of 6 to 50, for example from 10 to 40 or 15 to 25, residues.

A β-chemokine analogue which is capable of inducing ripening of the cervix may alternatively be used in the invention. The ability of an analogue to induce cervical ripening can be determined by testing. An analogue may be derived by modifying the amino acid sequence of a β-chemokine, for example one of the amino acid sequences set out in Table 1, or of a fragment of a β-chemokine.

The amino acid sequence of a β-chemokine or a fragment thereof may be modified by one or more amino acid substitutions and/or insertions and/or by an extension at either or each end. Typically there is a degree of homology of 75% or more between the amino acid sequence of the unmodified β-chemokine or β-chemokine fragment and the amino acid sequence of an analogue thereof. The degree of homology may be 85% or more or 95% or more.

Conservative amino acid substitutions can be made to the native sequence of a β-chemokine or β-chemokine fragment. Up to 15 such substitutions may be made, for example from 1 to 10 or from 2 to 6. One, two, three, four or five conservative substitutions may be made.

Candidate conservative substitutions are shown in Table 3 below. The symbols and abbreviations used in Table 3 are those recommended by the IUPAC-IUB Joint Commission on Biochemical Nomenclature, "Nomenclature and Symbolism for Amino Acids and Peptides, Recommendations 1983" J. Biol. Chem. 260 14–42 (1985). Other abbreviations employed are:

Nle: norleucine,
Aib: aminoisobutyric acid,
AdaA: β-adamantylalanine,
AdaG: α-adamantylglycine,
homo-Arg: L-homoarginine,
D-homo-Arg: D-homoarginine,
Acp: aminocaproic acid,
Chg: L-α-cyclohexylglycine,
allo-Thr: L-allothreonine,
Cha: β-cyclohexyl-alanine,
Orn: ornithine,
pyro-Glu: pyroglutamyl,
Met(O) and D-Met(O): the sulfoxides derived from L- and D-methionine respectively,
β-Ala: β:-alanine,
Acm: acetamidomethyl,
L-Dopa: 3-(3,4-dihydroxyphenyl)-L-alanine, and
Bpa: 4-benzoyl-phenylalanine.

The physicochemical character of the original sequence can thus be preserved, i.e. in terms of charge density, hydrophobicity/hydrophilicity, size and configuration. A molecule substantially similar to the native β-chemokine or β-chemokine fragment can thus be produced. Similarity can be determined by testing, for example for chemotaxis in relation to monocytes. In the case of analogues of the preferred individual β-chemokines noted above, the analogues can be tested for the in vitro biological functions shown in Table 2.

Analogues may be derived also by insertion into the amino acid sequence of a β-chemokine or β-chemokine fragment of, for example, up to 10 amino acid residues such as from 1 to 5 residues. Analogues may be derived by provision of extensions at the C-terminus or N-terminus of a β-chemokine. Such extensions may be up to 10 amino acid residues long, for example from 1 to 5 residues long. The residues for insertion and/or addition as an extension are selected such that the resulting analogue has substantially similar activity as the β-chemokine or, as appropriate, β-chemokine fragment from which it is derived.

The invention also provides a method of inducing ripening of the cervix of a female mammal in need thereof, which method comprises administering to the female mammal an effective amount of a MCP-1 or a functional derivative thereof. The invention applies to humans and to any other mammal which has a fundamental parturition mechanism similar to that of humans, in that cervical ripening is required.

Administration may be effected in any way in which, directly or indirectly, it will reach the cervix. Thus, the active compound can be conveniently applied intravaginally or directly to the cervix, e.g. typically as a gel or cream. It can also be injected into the cervix. It can also be applied extra-amniotically, i.e. between the uterine wall and the amniotic sac, using a catheter.

A safe and effective amount of a MCP-1 or functional derivative thereof is administered. The amount applied will depend upon a number of factors such as the host, the mode of administration and the purpose. A dosage normally would be from 0.001 to 20 mg, such as from 0.01 to 20 mg, per cervix. Administration can be all at once, in divided doses or by slow release.

The time of the application will depend on a number of factors including the purpose for which the MCP-1 or functional derivative thereof is being given. If being given in connection with a birth, the time will depend upon the course of the labour. In birth it is desirable to ensure that the cervix is ripened before the myometrial contractions have begun or are about to begin.

The MCP-1 or a functional derivative thereof may be used in connection with birth or abortion. In this situation of pregnancy, the cervix is pre-treated. The hormones during pregnancy alter the cervix which is then inclined to respond effectively to other stimulants. The MCP-1 or functional derivative thereof can also be used in connection with surgical procedure and diagnostic procedure. Therefore, they can be used for the following indications:

(A) induction of labour at term (time of ordinary birth, optionally combined with sequential treatment with oxytocin or similar agents), (B) induction of labour in connection with a pathological pregnancy (e.g. fetal malformation) (preferred second trimester abortion), (C) induction of labour in connection with intrauterine fetal death, (D) induction of abortion (preferred second trimester abortion), (E) induction of preterm labour, (F) induction of cervical ripening of a non-pregnant female or pregnant female to assist for surgical or diagnostic procedure, and (G) induction of cervical ripening for female to be treated by in vitro fertilisation.

The MCP-1 or functional derivative thereof can therefore be used in assisting labour, whether in a natural or surgically assisted procedure. The MCP-1 or functional derivative is additionally useful in removing an unwanted fetus, e.g. in an abortion procedure, which may also be natural or surgically assisted.

In addition MCP-1 or a functional derivative thereof can be used to soften the cervix to facilitate other operations such as assisted conception procedures and endoscopic examination. The procurement of a softened cervix may allow these and other procedures to be performed without anaesthetic.

The MCP-1 or functional derivative thereof is typically formulated as a pharmaceutical composition comprising also a pharmaceutically acceptable carrier or diluent. Certain compositions form part of the invention, notably gel or cream formulations comprising MCP-1 or a functional derivative thereof and a gel-forming or cream-forming vehicle, respectively. The gels and creams may contain any suitable aqueous oleaginous substance as the vehicle. Alternatively, the MCP-1 or functional derivative thereof may be formulated as softenable capsules, liposomes, suppositories, a slow-release or delayed-release formulation, or an aqueous solution, e.g. a saline or protein-containing solution.

Gels will usually be of hydrophilic polymers such as cross-linked polyethylene glycol, cross-linked starch or polyvinyl pyrrolidone. The gel may be a syringeable gel. Capsules can be made of a polymer which is softenable by body heat, such as gelatin or a polymer which slowly dissolves in body fluids. Many types of slow release compositions are well known, e.g. of the matrix type (see, for instance, U.S. Pat. No. 3,851,648) or membrane type.

The MCP-1 or functional derivative may be co-administered with a substance which induces myometrial contractions, for example a prostaglandin such as prostaglandin $E_2$, or a uterotonic effective compound. Such co-administration can be used in connection with birth or abortion. Uterotonic effective compounds are described in EP-A-0 214 924 and EP-A-0 184 471. A preferred uterotonic effective compound is oxytocin. The invention thus also provides:

- a combination of (i) a substance which induces myometrial contractions and (ii) MCP-1 or a functional derivative thereof for manufacture of a medicament for cervical ripening in a female mammal;
- a product containing (i) a substance which induces myometrial contractions and (ii) MCP-1 or a functional derivative thereof as a combined preparation for simultaneous, separate or sequential use for cervical ripening of a female mammal; and
- a product containing (i) a uterotonic effective compound and (ii) MCP-1 or a functional derivative thereof as a combined preparation for simultaneous, separate or sequential use for cervical ripening of a female mammal.

The substance which induces myometrial contractions or uterotonic effective compound on the one hand and the MCP-1 or functional derivative thereof on the other hand can be administered by different pathways (for example gel and injection) and at different times (for example first MCP-1 or functional derivative thereof and after 6 to 48 hours oxytoxin).

The substance which induces myometrial contractions or uterotonic effective compound on the one hand and the MCP-1 or functional derivative thereof on the other hand can be presented separately packaged within a kit. However, the invention also provides a pharmaceutical composition which comprises (1) a MCP-1 or a functional derivative thereof; (2) a substance which induces myometrial contractions such as a prostaglandin, for example prostaglandin $E_2$; and (3) a pharmaceutically acceptable diluent or carrier. Such a composition can be in any of the forms referred to above or below. It may also include IL-8 in any of the forms described in WO 93/07976.

The following Examples illustrate the invention.

EXAMPLE 1

Endometrial Tissue

Endometrium was obtained, with the informed consent of the patient, from total abdominal hysterectomy for non-malignant causes. Small (approximately 2 mm×2 mm×1 mm) pieces of tissue were placed on sterilised polypropylene capillary matting at the liquid/air interface. Medium used was RPMI 1640 (Hyclone) containing 10% fetal calf serum (Gibco) penicillin (50 μg/ml) and streptomycin (50 units/ml) and gentamycin 5 μg/ml. Tissue was placed in culture in a 5% $CO_2$-in-air atmosphere within 30 minutes of collection. Six replicate wells per treatment were used. Tissue protein levels were determined by digestion of tissue in sodium hydroxide followed by calorimetric assay.

Choriodecidual Cells

Fetal membranes with attached decidua were obtained from elective caesarean section at full term; the area of membrane overlying the placenta was not used. Chorion was separated from amnion and chopped into 3–4 mm pieces and placed in a digestion flask with 300 ml of RPMI with Trypsin, 0.5% (w/v) and DNAase 20 mg/l. Tissue was digested for 40 minutes and filtered through 0.16 mm mesh nylon filter. Viability (trypan blue exclusion) of all cells was greater than 90%. Cells were plated in 1.7 cm diameter wells at 200,000 cells per well and incubated in an atmosphere of 5% $CO_2$ -in-air. Six replicate wells per treatment were used. Steroid treatment was commenced after seven days in culture. Data shown are from media collected between 24 and 72 hours after phorbol ester (Phorbol myristoyl acetate) treatment.

Progesterone, and medroxy progesterone acetate (MPA; 6a-methyl-17a-acetoxy pregn-4-ene-3,20-dione) were obtained from Sigma. Steroid stocks were kept in ethanol at 2 mg/ml and diluted in complete medium to give a 10 times concentrated solution. 10% of this working solution was added to incubation wells. The final concentration of ethanol was 0.02% and this concentration of ethanol was added to control wells. Steroids were used at $10^{-6}$ M in the wells.

MCP-1 Assay

MCP-1 produced in the wells was measured by a specific radioimmunoassay. Antisera (goat) against MCP-1 was purchased from R&D Systems, Oxford and used at an approximate dilution of 1:12500. Label was prepared by iodination (Chloramine-T) of human recombinant MCP-1 R&D Systems, Oxford, followed by chromatography on a carboxy methyl silica column. In relation to the endometrial tissue, where different weights of whole tissue were used, the results were expressed in terms of ng of MCP-1 per mg tissue per ml of solution. The results are shown below.

TABLE 4

MCP-1 release from endometrium explants
(ng/mg/ml) ± standard error of the mean

| | |
|---|---|
| Control | 14.2 ± 2.4 |
| with MPA | 5.6 ± 1.5 |
| with progesterone | 3.1 ± 1.4 |

TABLE 5

MCP-1 release from choriodecidual cells
(ng/mg/ml) ± standard error of the mean

| | |
|---|---|
| Control | 3.3 ± 0.6 |
| With MPA | 1.5 ± 0.4 |
| With progesterone | 0.8 ± 0.2 |

The results, which are only comparable for the same tissue, show that MCP-1 was produced in endometrium (the mucous membrane on the inside of the uterus) and also in the chorio-decidual tissue. Production was inhibited by progesterone, the hormone that maintains pregnancy. The proximity of chorio-decidual tissue to the cervix means that MCP-1 would be available to the cervix. As explained above, it may reasonably be assumed from this information that MCP-1 is useful in cervical ripening and therefore that such ripening can be induced or enhanced by administration of MCP-1 to the area of the cervix.

EXAMPLE 2

Twenty four females rabbits were divided into 4 equal groups. Each group consisted of 6 rabbits, 3 were not pregnant and 3 were pregnant. All animals were treated by vaginal suppositories containing either placebo (control) or 100 ng of MCP-1. MCP-1 was prepared from human fibroblast cells stimulated with poly I/poly C and purified. The MCP-1 was supplied by Toray Industries Inc. Kamakara, Japan and has chemotactic activity for macrophages at 0.1 to 1 ng per ml and induces calcium fluxes in THP-1 cells at 1 ng per ml. Each rabbit received one suppository daily for 1,2 or 3 days. Animals were sacrificed 24 h after the last dose. Dissected cervices were examined for consistency and dilatation using Hegar's dilators.

Histological sections were prepared and stained with hematoxylin and eosin (H&E) to study the pathological changes. Immunohistological staining for surface antigen RT-2 found in the rabbit leukocytes was carried out using anti-rabbit RT-2 monoclonal antibody (Cedarlane Laboratories Limited, Canada). The total numbers of leukocytes in 5 random fields of the connective tissue of each biopsy specimen were counted (magnification ×20).

Relative collagen concentration was assessed by staining with picrosirius red (Sirius red F3BA Chroma-Gesellschaft Schmid Gmbh, Germany), and validated as a histological method of determining the polymerized collagen concentration of tissues including that of the cervix.

The histological analysis was performed by measuring the optical density (% polarized light transmission) from 5 random fields of the connective tissue of each biopsy and the mean optical density was calculated. An image analyzer was employed for all histological measurements (Microscope: Olympus IMT-2, Video camera SIT C2400–80 and Computer analyzer system with ARGUS-100 Hamamatsu photonics). In picrosirius red staining, the greater the collagen concentration, the greater the birefringence, and hence the greater the percentage of light transmission.

In each cervix, 100 mg of connective tissue was cut, homogenized with phosphate-buffered saline and centrifuged. The supernatant fluid was collected and stored at −80° C. until used. Collagenase activity was measured in these cervical fluids using highly specific kits (Collagenase type I activity measurement, Yagai, Japan). Whereas elastase activity was measured by a specific chromogenic substrate for granulocyte elastase S-2484 (L-pyroglutamyl-L-prolyl-l-valine-P-nitranilide, KABI Diagnostic, Sweden). Elastase levels are shown in Table 3 and reflect neutrophil enzyme release.

Softening and dilation was observed in cervices treated by MCP-1. The effect of MCP-1 increased with time. Examination of histological sections showed a marked decrease in collagen content after application of MCP-1. Collagen bundles became loose and widely separated by the ground matrix. At the same time, blood vessels were dilated and crowded with leukocytes. Also, leukocytes were distributed in connective tissue around the blood vessels and below the glandular epithelium. A significant increase in leukocyte numbers invading the connective tissue was observed.

Measuring the optical density showed a significant decrease of relative collagen content in cervical tissues treated by MCP-1 (Table 6). Collagenase activity was significantly increased in the tested non-pregnant and pregnant cervices compared to the control group. Elastase activity (a measure of neutrophil enzyme release) was increased in cervical fluid in MCP-1-treated groups relative to the control groups (Table 6).

TABLE 6

Measures of cervical ripening in rabbits in response to MCP-1

| | OD (% transmission) = Relative collagen concentration | Elastase Activity (U/100 mg) |
|---|---|---|
| Non-pregnant Control | 55 ± 1.1 | 5 ± 2.8 |
| 1st Day | 41 ± 2.2 | 9 ± 2 |
| 2nd Day | 27.5 ± 1.5 | 10.5 ± 2 |
| 3rd Day | 15.5 ± 0.6 | 17.5 ± 4 |
| Pregnant Control | 32 ± 0.9 | |
| 1st Day | 22 ± 1.2 | |
| 2nd Day | 14 ± 0.6 | |
| 3rd Day | 10 ± 0.5 | |

EXAMPLE 3

Monocyte chemotactic peptide-1 (0.5 mg) in aqueous solution is added to 0.1 g of cross-linked starch and the polymer is allowed to absorb the solution. The preparation is then freeze-dried and stored dry. Before application by the physician, physiological saline is added to the polymer to give a gel of the required consistency for application by syringe. The gel is then squirted into the cervix by syringe.

TABLE 1

AMINO ACID SEQUENCES OF β-CHEMOKINES ARRANGED TO SHOW HOMOLOGY

| | | | | | |
|---|---|---|---|---|---|
| KSMQVPFSR QRHRKMLRHCPSKRK | CCFSFAEQEI | PLRAILCYRN | TSSI CSNEG.LIFKLKRGKE | ACALDTVGWV | I309 |
| QPDAINAPVT QDSMDHLDKQ | CCYNFTNRKI TQTPKT | SVQRLASYRR | ITSSKCPKEA.VIFKTIVAKE | ICADPKQKWV | MCP-1 |
| QPDSVSIPIT RDSMKHLDQI | CCFNVINRKI FQNLKP | PIQRLESYTR | ITNIQCPKEA VIFKTKRGKE | VCADPKERWV | MCP-2 |
| QPVGINTSTT QDFMKHLDKK | CCYRFINKKI TQTPKL | PKQRLESYRR | TTSHSCPREA VIFKTKLDKE | ICADPTQKWV | MCP-3 |
| SPYSSDTTP REYINSLEMS | CCFAYIARPL | PRAHIKEYFY | TSGK CNSPA VVFVTRKNRQ | VCANPEKKWV | RANTES |
| AMPGSDPPTA QEYVYDLELN | CCFSYTARKL | PRNFVVDYYE | TSSL CSQPA VVFQTKRSKQ | VCADPSESWV | MIP-1β |
| ASLAADTPTA QKVYSDLELS | CCFSYTSRQI A | PQNFIADYFE | TSSQ CSKPG VIFLTKRSRQ | VCADPSEEWV | MIP-1α |

TABLE 2

IN VITRO BIOLOGICAL FUNCTIONS OF β-CHEMOKINES

| Chemokine | Target cells | Effect |
|---|---|---|
| MCP-1 | Monocytes | chemotaxis |
| | | intracellular calcium influx |
| | | respiratory burst |
| | | expression of β2-integrins (CD11b/CD18 and CD11c/CD18) |
| | | production of IL-1 and IL-6 |
| | | augmentation of cytostatic activity |
| | | N-acetyl β-glucuronaminidase release |
| | T cells | chemotaxis |
| | Basophils | histamine release |
| | | leukotriene release |
| | | chemotaxis |
| | | intracellular calcium influx |
| | Stem cells | suppression of colony formation of progenitor cells |
| MCP-2 | Monocytes | chemotaxis |
| | T cells | chemotaxis |
| MCP-3 | Monocytes | chemotaxis |
| | T cells | chemotaxis |
| | Basophils | chemotaxis |
| | | release of histamine |
| | | release of leukotriene |
| | Eosinophils | chemotaxis |
| MIP-1α | Neutrophils | chemotaxis |
| | | oxidative burst |
| | | degranulation |
| | | lysosomal enzyme release |
| | Monocytes | chemotaxis |
| | | intracellular calcium influx |
| | T-cells | chemotaxis for CD8 + T lymphocytes |
| | Basophils | chemotaxis |
| | | release of histamine |
| | Eosinophils | chemotaxis |
| | | release of cationic protein |
| | Mast cells | chemotaxis |
| | Stem cells | proliferation of granulocyte-macrophage progenitor cells |
| | | suppression of immature progenitor cells |
| MIP-1β | Monocytes | chemotaxis |
| | | intracellular calcium influx |
| | T cells | chemotaxis for CD4 + T lumphocytes |
| | | promotion of adhesion to VCAM-1 |
| | Stem cells | inhibition of the effect of MIP-1α |
| RANTES | Monocytes | chemotaxis |
| | | intracellular calcium influx |
| | T cells | chemotaxis for CD4 + memory T cells |
| | Basophils | chemotaxis |
| | | release of histamine |
| | Eosinophils | chemotaxis |
| | | respiratory burst |
| | | release of cationic protein |
| I-309 | Monocytes | chemotaxis |

TABLE 3

CONSERVATIVE AMINO ACID REPLACEMENTS

| For Amino Acid | Code | Replace with |
|---|---|---|
| L-Alanine | A | D-Ala, Gly, Aib, β-Ala, Acp or delete |
| L-Arginine | R | D-Arg, Lys, D-Lys, homo-Arg, D-homo-Arg, Met, Ile, D-Met, D-Ile, Orn, D-Orn or delete |
| L-Asparagine | N | D-Asn, Asp, D-Asp, Glu, D-Gln, Glu, D-Gln or delete |
| L-Aspartic Acid | D | D-Asp, D-Asn, Asn, Glu, D-Glu, Gln, D-Gln or delete |
| L-Cysteine | C | D-Cys, S-Me-Cys, Met, D-Met, Thr, D-Thr or delete |
| L-Glutamine | Q | D-Gln, Asn, D-Asn, Glu, D-Glu, Asp, D-Asp or delete |
| L-Glutamic Acid | E | D-Glu, D-Asp, Asp, Ans, D-Asn, Gln, D-Gln or delete |
| L-Glycine | G | Ala, D-Ala, Pro, D-Pro, Aib, β-Ala, Acp or delete |
| L-Isoleucine | I | D-Ile, Val, D-Val, AdaA, AdaG, Leu, D-Leu, Met, D-Met or delete |
| L-Leucine | L | D-Leu, Val, D-Val, AdaA, AdaG, Leu, D-Leu, Met, D-Met or delete |
| L-Lysine | K | D-Lys, Arg, D-Arg, homo-Arg, D-homo-Arg, Met, D-Met, Ile, D-Ile, Orn, D-Orn or delete |
| L-Methionine | M | D-Met, S-Me-Cys, Ile, D-Ile, Leu, D-Leu, Val, D-Val or delete |
| L-Phenylalanine | F | D-Phe, Tyr, D-Thr, L-Dopa, His, D-His, Trp, D-Trp, trans-3,4 or 5-phenylproline, Ada-A, AdaG, cis-3,4 or 5-phenylproline, Bpa, D-Bpa or delete |
| L-Proline | P | D-Pro, L-1-thiazolidine-4-carboxylic acid, D-or L-1-oxazolidine-4-carboxylic acid or delete |
| L-Serine | S | D-Ser, Thr, D-Thr, allo-Thr, Met, D-Met, Met (O), D-Met (O) or delete |
| L-Threonine | T | D-Thr, Ser, D-Ser, allo-Thr, Met, D-Met, Met (O), D-Met (O), Val, D-Val or delete |
| L-Tyrosine | Y | D-Tyr, Phe, D-Phe, L-Dopa, His, D-His or delete |
| L-Valine | V | D-Val, Leu, D-Leu, Ile, D-Ile, Met, D-Met, AdaA, AdaG or delete |

I claim:

1. A pharmaceutical composition which comprises (1) a MCP-1 or functional derivative thereof, (2) a substance which induces myometrial contractions and (3) a pharmaceutically acceptable carrier or diluent.

2. A composition according to claim 1 wherein substance (2) is prostaglandin-E.

3. A composition according to claim 1 in the form of a gel, cream microcapsules, a slow or delayed release formulation or a sterile injectable solution or suspension.

4. A method of inducing ripening of the cervix of a female mammal in need thereof, which method comprises administering to the female mammal an effective amount of a MCP-1 or functional derivative thereof.

5. A method according to claim 4 wherein the MCP-1 or functional derivative thereof is administered in connection with human birth or abortion.

6. A derivative according to claim 4 wherein the MCP-1 functional derivative is another β-chemokine.

7. A method according to claim 4 wherein the MCP-1 or functional derivative thereof is co-administered with a substance which induces myometrial contractions or with a uterotonic effective compound.

8. A method according to claim 4 wherein the MCP-1 or functional derivative thereof is administered as a gel or cream comprising the MCP-1 or functional derivative thereof and a gel-forming or cream-forming vehicle.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
         (A) LENGTH: 73 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO: 1:

Lys Ser Met Gln Val Pro Phe Ser Arg Cys Cys Phe Ser Phe Ala Glu
    1               5                   10                  15

Gln Glu Ile Pro Leu Arg Ala Ile Leu Cys Tyr Arg Asn Thr Ser Ser
                    20                  25                  30

Ile Cys Ser Asn Glu Gly Leu Ile Phe Lys Leu Lys Arg Gly Lys Glu
                35                  40                  45

Ala Cys Ala Leu Asp Thr Val Gly Trp Val Gln Arg His Arg Lys Met
            50                  55                  60

Leu Arg His Cys Pro Ser Lys Arg Lys
    65                  70

(2) INFORMATION FOR SEQ ID NO: 2:

(i) SEQUENCE CHARACTERISTICS:
         (A) LENGTH: 76 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO: 2:

Gln Pro Asp Ala Ile Asn Ala Pro Val Thr Cys Cys Tyr Asn Phe Thr
    1               5                   10                  15

Asn Arg Lys Ile Ser Val Gln Arg Leu Ala Ser Tyr Arg Arg Ile Thr
                    20                  25                  30

Ser Ser Lys Cys Pro Lys Glu Ala Val Ile Phe Lys Thr Ile Val Ala
                35                  40                  45

Lys Glu Ile Cys Ala Asp Pro Lys Gln Lys Trp Val Gln Asp Ser Met
            50                  55                  60

Asp His Leu Asp Lys Gln Thr Gln Thr Pro Lys Thr
    65                  70                  75

(2) INFORMATION FOR SEQ ID NO: 3:

(i) SEQUENCE CHARACTERISTICS:
         (A) LENGTH: 76 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO: 3:

Gln Pro Asp Ser Val Ser Ile Pro Ile Thr Cys Cys Phe Asn Val Ile
    1               5                   10                  15

Asn Arg Lys Ile Pro Ile Gln Arg Leu Glu Ser Tyr Thr Arg Ile Thr

```
                    20                  25                  30
        Asn Ile Gln Cys Pro Lys Glu Ala Val Ile Phe Lys Thr Lys Arg Gly
                    35                  40                  45

Lys Glu Val Cys Ala Asp Pro Lys Glu Arg Trp Val Arg Asp Ser Met
        50                  55                  60

Lys His Leu Asp Gln Ile Phe Gln Asn Leu Lys Pro
        65                  70                  75
```

(2) INFORMATION FOR SEQ ID NO: 4:

(i) SEQUENCE CHARACTERISTICS:
        (A) LENGTH: 76 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 4:

```
        Gln Pro Val Gly Ile Asn Thr Ser Thr Thr Cys Cys Tyr Arg Phe Ile
        1               5                   10                  15

Asn Lys Lys Ile Pro Lys Gln Arg Leu Glu Ser Tyr Arg Arg Thr Thr
                    20                  25                  30

Ser His Ser Cys Pro Arg Glu Ala Val Ile Phe Lys Thr Lys Leu Asp
                    35                  40                  45

Lys Glu Ile Cys Ala Asp Pro Thr Gln Lys Trp Val Gln Asp Phe Met
        50                  55                  60

Lys His Leu Asp Lys Lys Thr Gln Thr Pro Lys Leu
        65                  70                  75
```

(2) INFORMATION FOR SEQ ID NO: 5:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 5:

```
        Ser Pro Tyr Ser Ser Asp Thr Thr Pro Cys Cys Phe Ala Tyr Ile Ala
        1               5                   10                  15

Arg Pro Leu Pro Arg Ala His Ile Lys Glu Tyr Phe Tyr Thr Ser Gly
                    20                  25                  30

Lys Cys Asn Ser Pro Ala Val Val Phe Val Thr Arg Lys Asn Arg Gln
                    35                  40                  45

Val Cys Ala Asn Pro Glu Lys Lys Trp Val Arg Glu Tyr Ile Asn Ser
        50                  55                  60

Leu Glu Met Ser
        65
```

(2) INFORMATION FOR SEQ ID NO:6:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
    Ala Met Pro Gly Ser Asp Pro Thr Ala Cys Cys Phe Ser Tyr Thr
    1               5               10                  15

Ala Arg Lys Leu Pro Arg Asn Phe Val Val Asp Tyr Tyr Glu Thr Ser
                    20              25              30

Ser Leu Cys Ser Gln Pro Ala Val Val Phe Gln Thr Lys Arg Ser Lys
                35              40              45

Gln Val Cys Ala Asp Pro Ser Glu Ser Trp Val Gln Glu Tyr Val Tyr
            50              55              60

Asp Leu Glu Leu Asn
    65

(2) INFORMATION FOR SEQ ID NO:7:

(i) SEQUENCE CHARACTERISTICS:
         (A) LENGTH: 70 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:7:

Ala Ser Leu Ala Ala Asp Thr Pro Thr Ala Cys Cys Phe Ser Tyr Thr
    1               5               10                  15

Ser Arg Gln Ile Pro Gln Asn Phe Ile Ala Asp Tyr Phe Glu Thr Ser
                    20              25              30

Ser Gln Cys Ser Lys Pro Gly Val Ile Phe Leu Thr Lys Arg Ser Arg
                35              40              45

Gln Val Cys Ala Asp Pro Ser Glu Glu Trp Val Gln Lys Val Tyr Ser
            50              55              60

Asp Leu Glu Leu Ser Ala
    65              70
```